United States Patent [19]

Golden

[11] 4,157,983

[45] Jun. 12, 1979

[54] PROCESS FOR PRODUCTION OF ENCAPSULATED WATER-DISPERSIBLE MATERIALS

[75] Inventor: Ronald Golden, Louisville, Ky.

[73] Assignee: Champion International Corporation, Stamford, Conn.

[21] Appl. No.: 819,830

[22] Filed: Jul. 28, 1977

[51] Int. Cl.$^2$ .................... B01J 13/02; A01N 17/00; A61K 9/58
[52] U.S. Cl. ......................................... 252/316; 8/79; 71/64 F; 106/308 N; 424/32
[58] Field of Search ................ 252/316; 424/32; 8/79; 106/308 N; 71/64 F

[56] References Cited

U.S. PATENT DOCUMENTS

| | | | |
|---|---|---|---|
| 3,669,899 | 6/1972 | Vassiliades et al. | 252/316 |
| 3,928,272 | 12/1975 | Brancato et al. | 162/166 X |

*Primary Examiner*—Richard D. Lovering
*Attorney, Agent, or Firm*—Evelyn M. Sommer

[57] ABSTRACT

Capsules containing water-dispersible material are disclosed. They are formed from an admixture of low HLB emulsifier, oily water-immiscible solvent for the emulsifier urea-formaldehyde prepolymer water-dispersible material, and water. This admixture is agitated to form a water-in-oil emulsion to which amphiphatic acidic catalyst is added to cure the prepolymer. After curing to solid form, the capsules are separated from the remaining liquid of the admixture.

10 Claims, No Drawings

PROCESS FOR PRODUCTION OF ENCAPSULATED WATER-DISPERSIBLE MATERIALS

BACKGROUND OF THE INVENTION

Encapsulation, and particularly micro-encapsulation, of various materials is a common means of providing such materials with a protective environment. Encapsulation with, for example, a urea-formaldehyde resin, provides such materials with an external matrix which insulates them—partially or completely—from conditions which might lead to their loss or to loss of their desired, active properties.

Typical examples of the use of encapsulation include protection of pigments or dyes to obtain improved bleed resistance, light fastness and compatibility. Water-soluble fire retardants are commonly encapsulated for use under conditions of high humidity. Pharmaceuticals, pesticides, herbicides, anti-fouling agents, catalysts and the like may be encapsulated in order to provide for controlled release of such materials over an extended period of time. Similarly, encapsulation of photographic emulsions provides improved characteristics; of opacifying agents such as titanium dioxide, for more efficient pigment particle spacing; and of other well known materials for improvement in their particular uses.

The specific methods of encapsulating these various materials vary widely, even where, for example a specific encapsulating material such as urea-formaldehyde prepolymer is utilized. Commonly, however, their basic approach includes the steps of:

A. forming an admixture of the material, emulsifier and prepolymer in a biphasic, liquid system;
B. emulsifying the admixture to form fine droplets containing the material;
C. curing the prepolymer about the dispersed droplets of material; and
D. separating the resultant, solid, encapsulated material from remaining liquid.

In general, these prior art methods suffer from one or more of a number of basic procedural drawbacks. Chief among them is the approach to curing of the encapsulating prepolymer.

In some procedures, strong acid catalysts have been added directly to the aqueous phase containing a water dispersible material. This addition is commonly performed even prior to admixture of the aqueous phase with the water-immiscible phase. In such procedures, polymerization commences early in the encapsulation process. This greatly limits the time for reaching a desired particle size because curing or gellation occurs too rapidly.

In other procedures, where a latent acid catalyst is added directly to the aqueous phase, the oil and water emulsion must be heated to activated the catalyst. This often leads to undesirable changes in particle size and even to a phase separation between the two liquids.

In addition, many water-dispersible materials flocculate under acidic or similar encapsulation conditions. The process consequently becomes difficult to control because the particle size of a material may grow unduly large prior to encapsulation and/or the material may lose its water-dispersible characteristic before encapsulation can be performed.

DESCRIPTION OF THE INVENTION

In accordance with the present invention, encapsulation is performed utilizing the basic approach of the prior art. In a first step, an admixture of emulsifier, oily water-immiscible solvent for the emulsifier, urea-formaldehyde prepolymer, the desired water-dispersible material to be encapsulated and water are combined. Ordinarily, this admixture of ingredients is formed by combining an aqueous solution of urea-formaldehyde prepolymer, the water-dispersible material (either in solid or water-dispersed form), and a solution of the emulsifier in its oily water-immiscible solvent. This procedure is not necessary, however, inasmuch as any manner or order of combination to form the admixture may be followed.

Once the admixture of all essential ingredients has been formed, it is subjected to agitation to produce a water-in-oil emulsion. Within the emulsion, the water-dispersible material may be found primarily within the discontinuous phase comprising aqueous droplets having diameters consonant in size with the eventual capsules. Curing of the urea-formaldehyde prepolymer within the emulsion then effects solidification of a resin matrix encapsulating the droplets so as to permit the separation of solid urea-formaldehyde capsules containing water-dispersible material.

The present invention improves upon prior art encapsulation processes through the timing and means by which the prepolymer is cured about the dispersed droplets in the water-in-oil emulsion. This curing is instituted by addition of an amphiphatic catalyst to the water-in-oil emulsion. By use of this particular class of catalysts and through addition at this late stage is the process, both greater control over the production and properties of the product capsules is obtained.

The term amphiphatic catalyst as used in this application includes acids which are hydrophilic and oleophilic in nature, in other words, these acids are soluble in both water and water-immiscible liquids. Specific examples of such acids include inorganic acids, such as hydrogen chloride, titanium tetrachloride, silicon tetrachloride, boron trihalide, boron trihalide complexes, and the like; oil-soluble sources of hydrogen halides, such as p-toluenesulfonyl chloride, benzenesulfonyl chloride, o-nitrobenzenesulfonyl chloride, and the like; oil-soluble acidic oxides, such as sulfur dioxide, phosphorous trioxide, chlorine tetraoxide, and the like; and oil-soluble organic acids, such as butyl acid phosphate, 2-chlorobenzoic acid, 4-biphenylcarboxylic acid, and the like.

By adding the catalyst directly to the water-in-oil emulsion, the onset of curing of the urea-formaldehyde prepolymer is closely controlled. Premature gellation or curing is thereby avoided. Also, polymerization cannot occur before the dispersed droplets have obtained the size (determined during emulsification) desired for the eventual product capsules.

Addition only after emulsification also permits greater flexibility in the timing of the encapsulation process. The prepolymer remains stable until addition, thus relieving the necessity for immediate progression from one step to the next in the sequence.

The catalyst alone may be added directly to the water-in-oil emulsion. It is preferred, in this case, that it be added as a solution or dispersion in oily water-immiscible solvent for the emulsifier or in another liquid immiscible therewith. This facilitates its distribution through the emulsion and obtains an initially higher distribution within the continuous oily phase of the emulsion. There, it will ensure optimum interfacial activity with the primarily aqueous phase prepolymer.

In the practice of the present invention, urea-formaldehyde prepolymer in virtually any ratio may be employed. It is preferred, however, that the urea to formaldehyde ratio be within the range of from about 1:1 to 1:2.75, most preferably about 1:2. Suitable prepolymer may simply be admixed with the other ingredients prior to emulsification. Alternatively, an aqueous solution of, for example, from 30 to 80%, preferably from 50 to 65%, of solids by weight may be combined with the remaining ingredients.

The amount of prepolymer used is a function of the type of product capsule to be produced. Ordinarily, however, a weight ratio of between 1000:1 to 1:1 of prepolymer to water-dispersible material is utilized, with the higher amounts to prepolymer preferably being provided for the more active materials encapsulated. A still lower ratio of down to about 1:10 may however be employed, especially where it is desired to adhere dispersed material particles without fully encapsulating them.

Other amino functional monomers can be utilized with prepolymer to effect modifications for which they are known in the art. Representative of such monomers include melamine, thiourea, guanidine, dicyanamide, aromatic amino compounds and other carbamic compounds commonly used in the manufacture of aminoplast resins. Similarly, the prepolymer may be modified through provision of conventional polyhydroxy or polyamino-functional compounds which may be either monomer or polymers. Typical examples of these compounds are trimethylolpropane, pentaerythritol, diethylenetriamine, polyvinyl alcohol, starches, modified starches, proteins, polyglycols, cellulose derivatives, alginates and the like.

The further modification of capsule characteristics and properties through inclusion of these amino and hydroxy compounds in the product resin is known for adapting them for specific purposes. Commonly, one or more of these compounds are added to make the resin more porous or subject to degradation. This provides for slow or controlled release of encapsulated material. Alternatively, others may be added to increase the strength and protection afforded by encapsulation.

The emulsifier utilized in accordance with the present invention should be one having a low HLB value. This value of hydrophile-lipophile balance is ordinarily within the range of between about 2 and 8, so as to insure the stability of the water-in-oil emulsion. Ordinarily, between about 0.4 and 1.6 parts of dry emulsifier is used for one part of water-immiscible liquid.

Suitable low HLB emulsifiers include stearic monoethanolamide, polyethylene oxide-polypropylene oxide block copolymers (such as Pluronic L122, Pluronic P123 produced by BASF-Wyandotte Co.), ethylene diamine derivatives of polyethylene oxide-polypropylene oxide block copolymers (such as Tetronic 1501, Tetronic 1502, produced by BASF-Wyandotte Co.), lanolin derivatives, sorbitol derivatives and other surfactants commonly used to promote the formation of similar emulsions. Like the prepolymer, the emulsifier may be combined directly with the other admixed materials to be agitated. It is again preferred, however, that the emulsifier be in dissolved form. Thus, it is usually added with the water-immiscible liquid utilized to form the emulsion's continuous phase.

The water-immiscible liquids utilized for water-in-oil emulsions may be any of those commonly used for this function. Generally, however, either aliphatic or aromatic low viscosity hydrocarbons, or derivatives thereof such as chlorinated hydrocarbons, are utilized as the oily water-immiscible solvent for the emulsifier. Representative examples of these solvents are aliphatic naphthas, such as Shell Sol 70, toluene, xylene, perchloroethylene, trichloroethane and the like. The amount of solvent may vary widely. In this connection, the only requirement is that there be enough present to ensure that, upon agitation, the emulsion product will be a water-in-oil one.

The material to be encapsulated may include any of the water-dispersible substances of mixtures thereof known in the art. They may be either soluble or, if insoluble, finely divided and dispersible in water. Suitable examples include those substances already enumerated above.

Once the liquid admixture of prepolymer, material to be encapsulated and other ingredients has been formed, it is subjected to agitation. Conventional agitation is continued until a water-in-oil emulsion having aqueous droplets of the desired product size is formed. Customarily, these droplets have an average diameter between about 0.1 to 100 microns, depending upon their ultimate use. Control of this diameter is afforded by conventional variation of emulsifier, oil solvent and like properties as well as through the degree of shear incident to agitation.

After formation of the emulsion, the catalyst is added. Ordinarily, the agitation is continued during and even after addition so as to retain control over the droplet size. This is not necessary, however, because reaction may proceed rapidly upon addition of catalyst and the resultant formation of resin about the droplets is sufficient substantially to preserve their sizes.

From about 0.5 to 10% of catalyst by weight of prepolymer is ordinarily added to the emulsion. This instigates polymerization, even under the preferred conditions of essentially ambient temperature (for example, between about 10° to 30° C.). Although higher temperatures may accelerate reaction, ambient ones are sufficient to permit essentially completed polymerization in as little as about ½ to 4 hours, preferably between about 1 to 2 hours.

After completion of the polymerization step, the capsules containing the water-dispersible material are separated from the remaining liquid. This may be done by simple filtration. Preferably, however, more complete separation is obtained. Accordingly, after filtration or a like mechanical removal, the capsules are dried so as to evaporate residually adherent solvent and the like.

Incident to separation, it is further preferred to neutralize the capsules so that their resin coating will be inert. This is conveniently done, for example, by treating the capsules—preferably after mechanical removal of liquid—with sodium hydroxide, sodium carbonate, alkanolamine or the like. Any subsequent further drying may then be performed to leave solid, dry capsules ready for their ultimate use.

In an optional embodiment, the capsules may be provided with a protective skin. This is most conveniently performed by applying an agent which is reactive with residual surface methylol or amino groups of the capsule resin. Suitable agents are polyfunctional or monofunctional isocyanates, acid chlorides, epoxides which extend the polymer chains; alkylating agents such as dimethyl sulfate; silyating agents such as substituted chlorosilanes and other conventional resin modifiers.

These agents, preferably in dispersed or dissolved form (such as in additional oil solvent), may be added to separated capsules or capsules in the emulsion medium. They react to modify the capsules by making them more compatible with other polymers or biological systems, to increase or decrease their hydrophobic characters—e.g. alter the water permeability of the capsule resin—, or provide other changes to surface properties of the resin in known manner so as to make it more desirable for a particular ultimate use.

The following are typical examples of means for practicing the present invention:

EXAMPLE 1

The mixture of 220 grams of 37% aqueous formaldehyde (containing 7% methanol), 80 grams of urea and 2 grams of melamine was adjusted to a pH of 8 with triethanolamine and held at a temperature of 70° C. for one hour to produce a prepolymer solution. After cooling the solution to 25° C., 24 grams of Hercules Monarch Green WD pigment (color index 74260) were dispersed in the solution in a Waring Blender. The pigmented prepolymer solution was then emulsified with a solution of 12 grams of Tetronic 1502 (a polyethylene oxide-polypropylene oxide block condensation product with ethylenediamine produced by BASF-Wyandotte Co., Wyandotte, Michigan) in 200 grams of xylene.

Fifty milliliters of 3.6 normal solution of sulfur dioxide in xylene were then added slowly to the water-in-oil emulsion to initiate an exothermic polymerization of the urea-formaldehyde. After one hour, the catalyzed emulsion was mixed with 500 grams of water, adjusted to a pH of 10 with 10% sodium hydroxide and heated under mild agitation to distill off the xylene component. The aqueous dispersion was then centrifuged and the dark green cake was redispersed in 2 liters of water and re-centrifuged. The separated cake was dried at 80° C. and ground to yield a powdery green product comprising encapsulated pigment. This product redispersed easily in both water and oily solvents.

EXAMPLE 2

Two hundred forty seven grams of 37% formaldehyde and 23.4 grams of water were combined and adjusted to a pH of 9.2 with sodium hydroxide. Ninety grams of urea were then added to the solution before heating it for one hour at 65° C. to produce a urea-formaldehyde prepolymer solution.

Fifty grams of concentrated phosphoric acid were added to a solution of 8 grams of Pluronic L123 (a polyethylene oxide-polypropylene oxide block copolymer of BASF-Wyandotte) in 150 grams of xylene under high agitation sufficient to effect emulsification. One hundred grams of the prepolymer solution were added to the emulsion under continuing high shear conditions. The droplets of acid and urea-formaldehyde prepolymer solution coalesced to yield spherical gel particles of between about 10 to 30 microns in diameter. After polymerization, solid particles were separated from the remaining solution. They were added to water, where it was observed that phosphoric acid was gradually released by leaching.

EXAMPLE 3

About 0.1 gram of methylene blue dye crystals were added to 100 grams of a prepolymer solution prepared as described in Example 1. The resulting dark blue solution was then emulsified with a solution of 8 grams of Tetronic 1502 in 100 grams of xylene. The emulsion was then further treated with 40 milliliters of a 5 normal xylene solution of sulfur dioxide to cause the exothermic polymerization of the urea-formaldehyde.

The catalyzed emulsion was mixed with 500 grams of water and the xylene stripped off under vacuum. The aqueous slurry was washed with water until the filtrate contained no blue color. The dried filter cake, which consisted of microscopic, spherical urea-formaldehyde resin capsules, still had the strong blue coloration of the methylene dye.

EXAMPLE 4

A prepolymer solution was prepared by heating 200 grams of 40% formaldehyde which had been adjusted to a pH of 7 with 1 normal sodium hydroxide to 70° C., adding 80 grams of urea and stirring at 70° C. for a further 3 hours. A 50% titanium dioxide dispersion was prepared from equal amounts of a water-dispersible, paper coating grade of anatase (Titanox AWD of National Lead Co.) and distilled water.

Fifty grams of the urea-formaldehyde prepolymer solution were mixed with 50 grams of the anatase dispersion and emulsified with a solution containing 4 grams of Pluronic L122, 2 grams of Span 80 (sorbitan monoleate of Atlas Chemicals Div., ICI America) and 1 gram of Pluronic L63 in 100 grams of toluene. Two milliliters of 50% butyl acid phosphate in toluene were added to the resultant water-in-oil emulsion, which was then stirred for 2 hours.

A sample of the catalyzed emulsion was dried and redispersed in water. Dark, opaque particles of encapsulated titanium dioxide were clearly visible within the microscopic resin capsules.

EXAMPLE 5

A urea-formaldehyde prepolymer solution was prepared as described in Example 1. Five grams of 2,4-dichlorophenoxy acetic acid herbicide were added to 100 grams of the prepolymer solution. Dilute sodium hydroxide solution was also added to just dissolve the acid without making the solution basic. Twenty grams of an 8% solution of a high molecular weight, 87% hydrolyzed polyvinyl alcohol (Covol 9740 of Corn Products Co.) were then added and the solution was agitated with a solution of 6 grams of stearic acid monoethanolamide in 100 grams of an aliphatic hydrocarbon oil (Shell sol 70, Shell Petroleum Co.) to form a water-in-oil emulsion.

Forty milliliters of a 4% normal solution of sulfur dioxide in xylene were added to the emulsion to cure the urea-formaldehyde resin and reconvert the herbicide to the acid form. Microscopic examination of the 20 to 50 microns urea-formaldehyde resin capsules thus produced revealed finely dispersed crystalline inclusions of the 2/4-dichlorophenoxyacetic acid. When contacted with water, these capsules were slowly leached of their herbicidal content to provide a controlled release suitable for agricultural applications.

EXAMPLE 6

Eighty grams of a 10% solution of high molecular weight, 87% hydrolyzed polyvinyl alcohol were mixed with 40 grams of a high-viscosity urea-formaldehyde prepolymer (PR703-78 of Borden Chemical Co.) and 5 grams of sodium bicarbonate. The aqueous solution was mixed under high shear with a solution of 6 grams of Tetronic 1502 in 100 grams of xylene to produce a water-in-oil emulsion. Twenty milliliters of a 4 normal solution of sulfur dioxide in xylene were added to the emulsion to release carbon dioxide bubbles and cure the urea-formaldehyde resin. Microscopic examination revealed that the separated capsules contained well defined gas vacuoles.

EXAMPLE 7

Ten grams of ammonium bromide were dissolved in 100 grams of urea-formaldehyde prepolymer (PR69 of Borden Chemical Co.). This solution was emulsified with a solution of 6 grams of Tetronic 1502 in 100 grams of xylene in a beaker utilizing a magnetic stirring bar to obtain large emulsion droplets. The resulting water-in-oil emulsion was treated with 40 milliliters of a 4 normal solution of sulfur dioxide in xylene and then stirred for 2 additional hours.

A portion of the catalyzed emulsion was filtered, washed with fresh xylene and dried. The solid capsules averaged between about 30 to 50 microns in diameter. A portion of this dried product was then slurried in distilled water and filtered. The filtrate exhibited only a slight haze when treated with silver nitrate.

To insure even greater isolation of the water-soluble bromide, some of the remaining dried capsules were treated further. Twenty grams of these capsules containing ammonium bromide were suspended in 100 grams of petroleum naphtha. One gram of dodecyl diisocyanate was added and the admixture stirred for 2 hours at 50° C. The microcapsules were then filtered off and dried.

When these further treated capsules were slurried in distilled water and then filtered, the filtrate exhibited virtually no haze when treated with silver nitrate. This was apparently due to a reaction between the added diisocyanate and the residual —OH and —NH groups on the surface of the microspheres to deposit a further water-resistant coating.

What is claimed is:

1. A process for encapsulation of water-dispersible material comprising preparing an admixture comprising:
    (a) low HLB emulsifier;
    (b) oily water-immiscible solvent for said emulsifier;
    (c) urea-formaldehyde prepolymer;
    (d) said water-dispersible material; and
    (e) water;

agitating said admixture to form a water-in-oil emulsion, adding amphiphatic acidic catalyst to said emulsion to cure said prepolymer and then separating the resultant, solid urea-formaldehyde capsules containing water-dispersible material.

2. The process of claim 1, wherein said prepolymer has a urea to formaldehyde ratio of between about 1:1 to 1:2.75.

3. The process of claim 2, wherein said prepolymer is dissolved in an aqueous solution at a concentration of between about 30 to 80% solids by weight.

4. The process of claim 1, wherein the admixture additionally contains a urea-formaldehyde modifying agent comprising a polyhydroxy or polyamino-functional compound.

5. The process of claim 1, wherein the prepolymer and water-dispersible material are in a weight ratio of between 1000:1 to 1:10.

6. The process of claim 1, wherein the emulsion contains dispersed, aqueous phase droplets having an average diameter of between 0.1 to 100 microns.

7. The process of claim 1, wherein the amphiphatic catalyst comprises sulfur dioxide, hydrogen chloride, titanium tetrachloride, silicon tetrachloride, boron trihalide, alkyl acid phosphate or carboxylic acid.

8. The process of claim 1, wherein the admixture agitated has a pH of greater than about 6.

9. The process of claim 1, wherein the admixture and emulsion are maintained at a temperature between about 10° and 30° C. until the prepolymer has been substantially cured.

10. The process of claim, wherein the water-dispersible material comprises an inorganic fire-retardant, pharmaceutical, dye, pigment, anti-fouling agent, catalyst, herbicide, pesticide or fertilizer.

* * * * *